United States Patent [19]

Scouten

[11] Patent Number: 4,595,489
[45] Date of Patent: Jun. 17, 1986

[54] REMOVAL OF PHENOLS FROM PHENOL-CONTAINING STREAMS

[75] Inventor: Charles G. Scouten, Westfield, N.J.

[73] Assignee: Exxon Research and Engineering Co., Florham Park, N.J.

[21] Appl. No.: 757,908

[22] Filed: Jul. 22, 1985

Related U.S. Application Data

[63] Continuation of Ser. No. 452,956, Dec. 27, 1982, abandoned.

[51] Int. Cl.$^4$ ............................................. C10G 17/00
[52] U.S. Cl. .................................... 208/263; 568/716
[58] Field of Search ......................... 208/263; 568/716

[56] References Cited

U.S. PATENT DOCUMENTS

| | | | |
|---|---|---|---|
| 1,608,075 | 11/1926 | Wallen | 568/716 |
| 2,152,722 | 4/1939 | Yabroff et al. | 208/263 |
| 2,168,078 | 8/1939 | Yabroff | 208/263 |
| 2,392,545 | 1/1946 | Pecket | 568/716 |
| 2,605,212 | 7/1952 | Lobban | 208/263 |
| 2,762,838 | 9/1956 | Toland | 568/716 |
| 2,911,360 | 11/1959 | Myers | 208/263 |
| 3,304,253 | 2/1967 | Lewis | 208/263 |
| 3,554,265 | 1/1971 | Milian | 568/716 |
| 4,256,568 | 3/1981 | Schlosberg et al. | 208/263 |
| 4,299,691 | 11/1981 | Dougherty et al. | 208/263 |
| 4,326,949 | 4/1982 | Schlosberg | 208/263 |

FOREIGN PATENT DOCUMENTS

| | | | |
|---|---|---|---|
| 1436373 | 3/1966 | France | 568/716 |
| 363330 | 6/1930 | United Kingdom | 208/263 |
| 0679569 | 8/1979 | U.S.S.R. | 568/716 |

OTHER PUBLICATIONS

El'Kind, Methods of Separation of Phenols, Bases and Hydrocarbons, 1957.

*Primary Examiner*—William R. Dixon, Jr.
*Assistant Examiner*—Cynthia A. Prezlock
*Attorney, Agent, or Firm*—Henry E. Naylor

[57] ABSTRACT

Disclosed is a process for recovering phenols from phenol-containing streams having at least a sufficient amount of water. The stream is contacted with a metal composition comprised of one or more oxides and/or hydroxides of metals capable of forming a metal phenate with the phenols of the stream. The resulting metal phenates are separated from the stream and are treated with steam at a temperature from about 250° C. to about 450° C., thereby producing phenols, and hydroxides of the metals of the phenate.

11 Claims, 2 Drawing Figures

REMOVAL OF PHENOLS FROM PHENOL-CONTAINING STREAMS

This application is a continuation of application Ser. No. 452,956, filed 12/27/82, now abandoned.

FIELD OF THE INVENTION

The present invention relates to the removal of phenols from phenol-containing streams by use of metal oxides and/or hydroxides whereupon the resulting metal phenate is heated at relatively low temperatures in the presence of steam to recover the phenol and the hydroxide of the metal of the metal phenate.

BACKGROUND OF THE INVENTION

The presence of phenols in various hydrocarbonaceous streams is troublesome. For example, the presence of phenols in liquids produced from coal causes instability of these liquids over a period of time by increasing the viscosity, the color intensity, and causing the separation of resinous materials. Moreover, without extensive hydrotreatment, coal liquids are generally not compatible with petroleum liquids of comparable boiling point. Thus, solids separation caused largely by high concentrations of phenols, leads to severe operability problems for coal/petroleum liquid blends. Furthermore, hydrodesulfurization and hydrodenitrogenation of coal liquids are required prior to reforming into motor gasoline. These steps would require a relatively large consumption of hydrogen for the phenol-rich coal liquids because of the extensive deoxygenation of phenols to water.

Various methods for removing these troublesome phenols from hydrocarbonaceous streams are taught in the art. For example, it is taught in U.K. Pat. No. 494,450 that weakly acid-reacting organic substances such as phenols, can be separated from hydrocarbonaceous streams by use of alkali metal or alkaline-earth metal oxides or hydroxides in the presence of an auxiliary agent such as an aliphatic polar compound. It is taught in U.S. Pat. No. 4,256,568, which is incorporated herein by reference, that phenols react with these oxides and hydroxides resulting in the formation of metal phenates, which are easily separated from the purified stream. Further, it is taught in Ges. Abhandl. Kenninis Kohle, Vol. 4, pp. 237–63 (1919), that certain metal phenates, such as calcium phenoxide, can be heated in the presence of carbon dioxide to yield phenols and calcium carbonate.

Still another method for separating such phenols is taught in U.S. Pat. No. 4,256,568, which method comprises treating a phenol-containing stream, such as a coal liquid, with a multivalent metal oxide and/or hydroxide. The resulting hydroxy metal phenate is then pyrolyzed to a temperature of about 650° C. to recover the phenols and an oxide of the multivalent metal.

Another method is disclosed in U.S. Pat. No. 4,299,691 which also employs a multivalent metal oxide and/or hydroxide for removal of phenols from phenol-containing hydrocarbonaceous streams. The resulting hydroxy metal phenates are then reacted with one or more $C_1$ to $C_{10}$ aliphatic alcohols or $C_7$ to $C_{16}$ arylalkyl primary alcohols.

Although some of these methods are commercially feasible in various industries, there is still a need to develop a process for removing, from hydrocarbonaceous streams, troublesome phenols and recovering the phenols and a metal hydroxide in a more efficient and inexpensive way.

SUMMARY OF THE INVENTION

In accordance with the present invention, phenols are removed from phenol-containing streams and the phenols are regenerated by a process which comprises: (a) contacting the stream with one or more metal oxides or hydroxides which are capable of forming a metal phenate with the phenols of the stream, wherein the stream is contacted at a temperature below the decomposition temperature of the resulting metal phenate or the temperature at which detrimental thermal degradation of the stream occurs; (b) separating the resulting metal phenate from the stream; and (c) treating the metal phenate with steam at a temperature from about 250° C. to about 450° C. thereby forming phenols and hydroxides of the metal of the phenate.

In preferred embodiments of the present invention, the stream is a phenol-containing hydrocarbonacous stream, and the metal composition is an alkali metal hydroxide employed in a sufficient concentration so that at least 15% of the total phenols present are removed from the stream.

In other preferred embodiments of the present invention the phenol-containing hydrocarbonaceous stream is a coal liquid and the metal is selected from the group consisting of sodium and potassium and the resulting metal phenate is contacted with steam at a temperature of about 350° C.

DETAILED DESCRIPTION OF THE INVENTION

Figure 1:
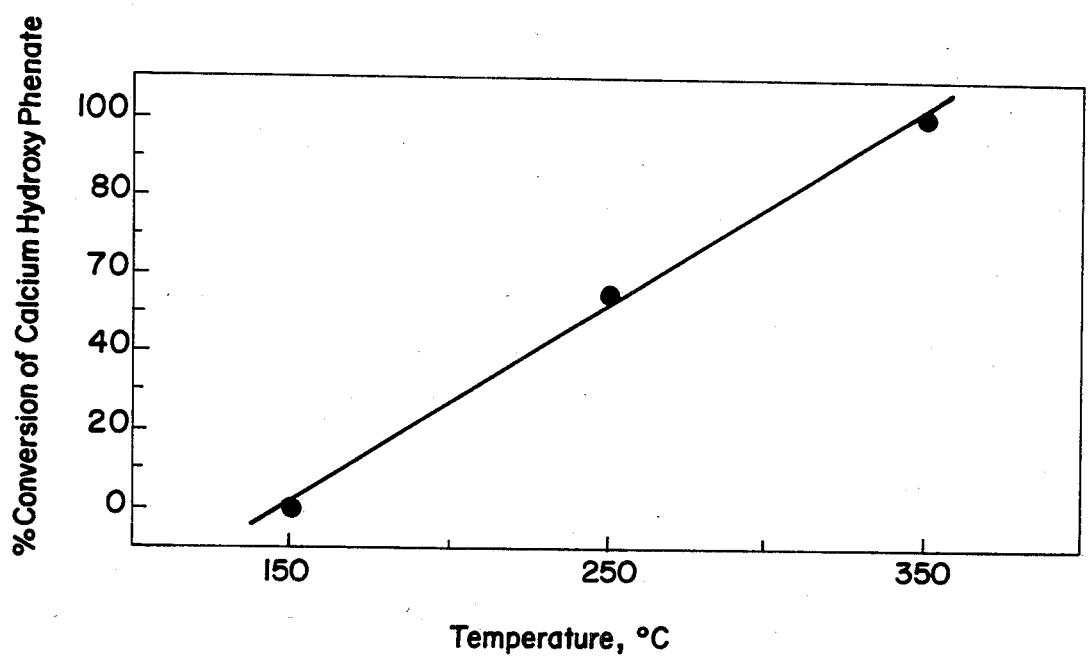
FIG. 1 is a plot of the amount of phenols recovered from calcium hydroxy phenate at various temperatures for a given period of time and at a molar ratio of water to calcium hydroxy phenate of 12 to 1.

Phenol-containing hydrocarbonaceous streams which can be treated according to the present invention include, but are not limited to, those streams resulting from the processing of coal, petroleum, and those existing as impurities in such parent streams as linear paraffins.

The term phenol-containing hydrocarbonaceous stream means a hydrocarbonaceous stream containing measurable amounts of phenol compounds in which one or more hydroxyl groups are attached to an aromatic ring and where the aromatic ring may also contain a heteroatom (e.g. nitrogen in a pyridine ring). Non-limiting examples of such phenol compounds include phenol itself, the cresols, xylenols, recorcinol, naphthols, 8-hydroxyquinoline and 4-hydroxyquinoline. The phenol-containing hydrocarbonaceous stream, exclusive of the phenol compounds, also contains at least 25 wt.% of compounds containing carbon and hydrogen, though other atoms (e.g. nitrogen, oxygen, sulfur) may also be present.

The stream must also contain a sufficient amount of water so that metal phenates will form when the stream is contacted with the metal oxide or hydroxide composition. The term, sufficient amount of water, as used herein, means at least that amount of water which would allow the formation of metal phenates within two hours from the time the stream is contacted. If the stream is substantially dry, or free of water, at least a sufficient amount of water must be added.

The present invention is not dependent on any particular method of producing the phenol-containing stream. For example, if the stream is a hydrocarbonaceous stream any coal liquid which contains phenols can be treated regardless of the way it was produced. Nonlimiting examples of types of processes for producing coal liquids include pyrolysis, solvent refining, direct hydrogenation with or without a catalyst, catalytic or noncatalytic hydrogenation in the presence of a non-hydrogen donor solvent and catalytic or non-catalytic liquefaction by a hydrogen donor solvent method. Furthermore, waste water streams which contain phenols may also be treated in accordance with the present inventions.

Although not wishing to be limited hereby, one preferred method for obtaining coal-liquids is the Exxon Donor Solvent (EDS) process for the liquefaction of coal which is described in U.S. Pat. No. 3,617,513 and incorporated herein by reference. Briefly stated, the EDS process involves the formation of a slurry of coal in a hydrogen-donor solvent, such as tetralin, and maintained at elevated temperatures of about 260° C. to 370° C. under agitation. Holding the coal at these temperatures causes the coal to disintegrate and dissolve without the breaking of a significant number of coal covalent bonds, thereby assuring only a limited amount of free radical formation. The slurry is held at these temperatures, under agitation, until the convertible portions of the coal are substantially uniformly dispersed in the hydrogen-donor solvent. When suitable dispersion is indicated, for example, by viscosity measurements conducted on the slurry, the temperature of the slurry is increased to bond-breaking, or depolymerization, temperatures, generally above about 370° C. Pressures effective to maintain the dispersant slurry substantially in the liquid phase, generally about 350 p.s.i.g. to 3500 p.s.i.g. are employed. In this second temperature stage, the dissolved coal particles are well dispersed in the hydrogen-donor solvent and the chance of a hydrogen-donor stabilization of free radicals generated by bond-breaking is maximized. At the same time, the chance for free radicals to combine with one another to produce undesirable molecules is minimized. The dispersed slurry is maintained at elevated temperatures, above about 370° C., until a predetermined conversion of the coal is obtained. The liquid product, which contains phenols, is then distilled, hydrogenated, the gases drawn off, and the bottoms removed for coking and gasification.

In accordance with the present invention, the phenol-containing stream is treated with one or more oxides and/or hydroxides of metals capable of forming a metal phenate with the phenols of the stream. Oxides and hydroxides of both monovalent metals, preferably the alkali metals, sodium and potassium; and multivalent metals, such as the alkaline-earth metals, are suitable for use herein: as long as they are capable of forming metal phenates with the phenols of the treated stream. The choice of the one or more metal oxides or hydroxides employed herein is dependent on such factors as the desired final level of phenols-content of the stream, the reactivity of the particular phenol compounds to the metal, and the type of phenol one wishes to separate.

For example, multivalent metal oxides and hydroxides are more reactive with the less sterically hindered phenols and therefore can be used to selectively remove such phenols, leaving most of the more sterically hindered phenols in the stream. On the other hand, oxides and hydroxides of monovalent metals, such as the alkali metals, will remove phenols without preference to steric factors. Consequently, if a stream contains both sterically hindered and non-hindered phenols, and if it is predetermined to remove substantially all of the phenols regardless of steric hindrance, then an oxide and/or hydroxide of an alkali metal would be employed. For purposes herein, the term, metal phenate, also includes hydroxy metal phenates which result from the reaction of certain multivalent metal oxides and hydroxides with phenols of the stream.

In the practice of the present invention, the stream is contacted at a temperature below the decomposition temperature of the resulting metal phenate. This is generally from about room temperature (20° C.) to either the decomposition temperature of the resulting metal phenate or the temperature at which detrimental thermal degradation of the stream occurs, whichever temperature is lower. For example, when calcium is the metal of the oxide or hydroxide used herein, the decomposition temperature of its resulting hydroxy calcium phenate is about 450° C. Detrimental degradation of the stream, as used herein means that when the stream reaches a certain elevated temperature, degradation reactions, such as polymerization leading to an increase in high boiling fractions, cracking leading to low value gaseous products, and coke formation leading to fouling, occur to such a degree that the overall chemical properties of the stream are adversely affected. The decomposition temperature of any resulting metal phenate, as well as the temperature at which detrimental thermal degradation of the stream occurs, can be easily determined by one having ordinary skill in the art and further elaboration is therefore not necessary.

The amount of metal composition needed in the practice of the present invention is dependent on the amount of metal required to react with a predetermined amount of the phenols of the stream. Although it may be desirable to remove as much of the phenols from the stream as possible, one may wish to remove only a certain minimum amount based on economic considerations.

The concentration of phenols in the hydrocarbonaceous stream can be determined by conventional analytical methods such as non-aqueous titration. The amount of multivalent metal needed to remove a predetermined amount of phenols can be expressed as the mol ratio of metal (as the oxide and/or hydroxide) to phenolic oxygen (in the feed stream). The preferred mol ratio of metal to phenolic-oxygen needed herein is that ratio which, when the metal oxides and/or hydroxides are contacted with the stream, will assure the removal of at least about 15 wt.% of the phenols from the feed stream at a temperature of about 25° C. for a contact time of about 90 minutes. The wt.% of phenol removal is based on the total weight of phenols in the stream.

It will be noted that because the activity of some metals is greater than that of other metals under a given set of conditions, less of the more active metal, for a given amount of phenols in the feed stream, will be required to remove a predetermined amount of the phenols from the stream. For example, at a temperature of 25° C. and a contact time of 90 minutes, about 17 wt.% of phenols are removed from a phenol-containing coal liquid using zinc hydroxide at a metal to oxygen mol ratio of 1.0; whereas, at the same temperature and metal to oxygen mol ratio, about 72 wt.% of phenols are removed from the same coal liquid when calcium hydroxide is used. The relative activity of one metal to another is known in the art and the ratio of any given metal to oxygen can be determined by either routine experimentation or calculation by one having ordinary skill in the art.

In order to achieve a high percentage of phenol removal with any metal oxide or hydroxide, a multistage process can be used. For example, at a calcium to oxygen mol ratio of 0.2, a contact time of 90 minutes, and at a temperature of 25° C., 48 wt.% removal of phenols from a coal liquid is achieved. If the treated coal liquid is contacted a second time at the same mol ratio, time, and temperature conditions as the first stage, an overall 77 wt.% removal of phenols is achieved. Therefore, it may be desirable to contact the liquid effluent from a previous stage many times over to effect substantially total removal of the phenols from the stream. For example, after initial contact of the stream with the metal composition, the treated stream is separated from the resulting metal phenate and passed along to another stage for contact with additional metal composition. This sequence can be repeated as often as practical and desirable.

It may be desirable from an energy savings point of view that the phenol-containing hydrocarbonaceous stream be at elevated temperatures when contacted with the metal composition. In this context, elevated temperatures means temperatures greater than room temperature but lower than the decomposition temperature of the resulting metal phenate. Generally, the phenol-containing feed stream will result from a chemical, petroleum, or coal process and will exit such process at elevated temperatures whereupon it can be treated directly with the metal composition as long as the temperature of the stream is lower than the decomposition temperature of the resulting metal phenate. Therefore, the temperature of the phenol-containing feed stream may be dependent on the source and process for its production and may have to be cooled to a lower temperature before treatment.

Although not wishing to be limited by theory, it is believed that the multivalent metals suitable for use herein form a hydroxy metal phenate with the phenol compounds contained in the hydrocarbonaceous stream. These hydroxy metal phenates can undergo intramolecular proton transfer. For example, if calcium hydroxide were used as the multivalent metal composition to remove phenols according to the present invention, it is believed that the following hydroxy metal phenate and reaction would result:

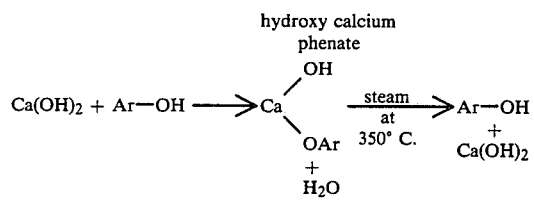

where Ar—OH represents a phenol compound or phenolic functionality in the hydrocarbonaceous stream. As shown above, upon contacting the hydroxy metal phenate with steam, the phenol compound is regenerated and a hydroxide of the multivalent metal is produced. This hydroxide can be recycled in a continuous process. For purposes of the present invention, the terms water and steam are sometimes used interchangeably.

In contrast to the above, if a monovalent metal composition, such as sodium or potassium oxide or hydroxide, is used for removal of phenols from a phenol-containing stream, the following salt and reaction would result:

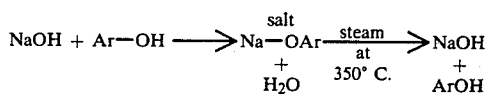

The above reactions show that both monovalent and multivalent metal compositions, which form metal phenates with the phenols of the stream are capable of regenerating the phenols and a metal hydroxide when treated with steam at a temperature of about 350° C.

It will be noted that, if present, carboxylic compositions may also be removed from the hydrocarbonaceous stream when treated according to the present invention.

One preferred method of the present invention for removing phenols from a stream is a continuous stirred tank reactor process which comprises contacting a phenol-containing hydrocarbonaceous feed stream with a predetermined concentration of a composition comprised of a metal oxide, metal hydroxide, or both, which metal compositions are capable of forming metal phenates with the phenols of the streams. This metal composition can contact the hydrocarbonaceous stream as either a solid or as an aqueous slurry containing the solid metal composition, if the metal is a multivalent metal. It is preferred that the hydrocarbonaceous stream be contacted with only solid particles of the multivalent metal composition so as to eliminate an aqueous phase.

Another preferred method for removing phenols is the use of a continuous extraction column with a liquid separator.

As previously discussed, the amount of metal composition contacting the stream is dependent on, among other things, the desired mol ratio of metal to phenolic-oxygen in the stream. For purposes of this invention, it is preferred that the mol ratio be at least that which will remove at least 15 wt.% of phenols from the stream. The metal composition and stream are thoroughly mixed to assure contact of the phenols with the metal composition. The phenols in the stream react with the metal composition, thereby forming a metal phenate. The metal phenate is separated from the stream by any conventional method and the hydrocarbonaceous effluent portion of the stream is passed along for further processing, further contacting with additional multivalent metal compositions, or such treatment as hydrofining. The metal phenate is removed and dried and any residual portions still containing phenolic functionality can be recycled to the feed stream. The dried metal phenate is treated with steam at a temperature from about 250° C. to 450° C., preferably from about 350° C. to 450° C. for an effective amount of time, thereby generating phenols as well as metal hydroxides. The phenols are collected and the metal hydroxides are recycled to the hydrocarbonaceous feed stream. Of course, multistage processing can be performed until the desired level of phenol removal is achieved.

Other methods which can be used in practicing the present invention for removing phenols from a hydrocarbonaceous stream, are fluidized or fixed bed processes using phenol sorbent materials. Suitable phenol sorbent materials include basic ceramics sorbents such as barium titinate, calcium titinate, calcium aluminate cement, and the like.

Other conventional solid/fluid processes can also be used. Non-limiting examples of such other processes include cyclic fluid bed, tube flow reactor, and moving bed processes.

The presence of the metal phenate, which is formed during the practice of the present invention is supported by conventional elemental analysis. That is, the amount of carbon, hydrogen and metal for each metal phenate can be calculated empirically, then substantiated by elemental analysis.

The following examples serve to more fully describe the present invention. It is understood that these examples in no way serve to limit the true scope of this invention, but rather, are presented for illustrative purposes.

EXAMPLES 1–4

Various multivalent metal oxides were used to extract phenols from a phenol-containing naphtha cut derived from a coal liquefaction process and containing a sufficient amount of water. The naphtha cut contained 1 mmol of oxygen/gm of naphtha, which oxygen is essentially all present as phenols. Concentrations of oxides were used to give a mol ratio of metal in the oxide to phenolic oxygen in the naphtha cut of 1.0. The naphtha cut in each instance was contacted for 90 minutes with the multivalent metal oxide at a temperature of 25° C. A hydroxy metal phenate resulted and was separated from the treated naphtha cut. The amount of phenols removed was determined by gas chromatography wherein the phenol content of the non-treated naphtha was compared to that of the treated naphtha. The results are set forth in Table I below:

TABLE I

| | Effect of Metal Atom on Removal of Phenols When Used in Oxide Form | |
|---|---|---|
| Ex. | Metal Ion | Wt. % of Phenol Removal |
| 1 | $Ca^{++}$ | 49 |
| 2 | $Sr^{++}$ | 65 |
| 3 | $Ba^{++}$ | 100 |
| 4 | $Ni^{+++}$ | 25 |

The above table shows that at a mol ratio of metal to phenolic-oxygen of 1, at a temperature of 25° C. and for a contact time of 90 minutes, the oxides of Ca, Sr, Ba and $Ni^{3+}$ are able to remove at least 25 wt.% of the phenols from the phenol-containing naphtha stream. The weight percent of phenol removed is based on the total weight of phenols in the untreated naphtha stream.

COMPARATIVE EXAMPLES A–D

For comparative purposes, various multivalent metal oxides, other than those of Examples 1–4, were used according to the conditions set forth in Examples 1–4. The results are shown in Table II below:

TABLE II

| | Effect of Metal Atom on Removal of Phenol When Used in Oxide Form | |
|---|---|---|
| Ex. | Metal Ion | Wt. % of Phenol Removal |
| A | $Mg^{++}$ | 5 |
| B | $Zn^{++}$ | 9.8 |

TABLE II-continued

| | Effect of Metal Atom on Removal of Phenol When Used in Oxide Form | |
|---|---|---|
| Ex. | Metal Ion | Wt. % of Phenol Removal |
| C | $Ni^{++}$ | 9 |
| D | $Ce^{4+}$ | 3 |

The above table shows that not all multivalent metal oxides are capable of removing at least 15 wt.% of phenols from the untreated naphtha cut.

EXAMPLES 5–10

Various multivalent metal oxides were used to remove phenols from the same naphtha cut and under the same conditions set forth in Examples 1–4 except, a stoichiometric amount of water was added to completely (hydrate) convert the metal oxide to the corresponding hydroxide. The results are set forth in Table III below.

TABLE III

| | Effect of Metal Atom on Removal of Phenols When Used in Hydroxide Form | |
|---|---|---|
| Ex. | Metal Ion | Wt. % of Phenol Removal |
| 5 | $Ca^{++}$ | 72 |
| 6 | $Sr^{++}$ | 99 |
| 7 | $Ba^{++}$ | 100 |
| 8 | $Zn^{++}$ | 17 |
| 9 | $Ni^{++}$ | 15 |
| 10 | $Ni^{+++}$ | 53 |

Table III shows, that generally, the multivalent metal hydroxide is preferred over the corresponding oxide because of its increased phenol removal capabilities. Although when barium is the multivalent metal, substantially all of the phenols are removed with either the oxide or hydroxide form.

COMPARATIVE EXAMPLE E

Comparative example D was repeated except a stoichiometric amount of water was added to completely (hydrate) convert cerium oxide to cerium hydroxide during phenol removal. After analysis by gas chromatography, it was found that the amount of phenol removal for cerium hydroxide was 7 wt.% vs. 3 wt.% for the corresponding oxide. This shows that even the hydroxide form of some multivalent metals is incapable of removing at least 15 wt.% of the phenols from a phenol-containing naphtha stream.

EXAMPLES 11–18

Various mol ratios of calcium, in its hydroxide form, to oxygen, in the naphtha cut, were used to remove phenols from the naphtha stream of Examples 1–4. These runs were performed at 25° C. for a 90 minute contact time in either 1 or 2 stage processes as indicated below. That is, if the process was a two stage process, the naphtha stream (treated or untreated depending on the stage) was contacted with calcium hydroxide for 90 minutes in each stage. The results are set forth in Table IV below.

TABLE IV

| Comparison of Removal Efficiencies for 1 and 2 Stage Batch Processes at Various M/O Values | | |
|---|---|---|
| Ex. | M/O Ratio | # of Stages | Wt. % of Phenol Removal[a] |
| 11 | 0.1 | 1 | 32 |

TABLE IV-continued

Comparison of Removal Efficiencies for 1 and
2 Stage Batch Processes at Various M/O Values

| Ex. | M/O Ratio | # of Stages | Wt. % of Phenol Removal[a] |
|---|---|---|---|
| 12 | 0.1 | 2 | 54 |
| 13 | 0.2 | 1 | 48 |
| 14 | 0.2 | 2 | 77 |
| 15 | 0.4 | 1 | 61 |
| 16 | 0.4 | 2 | 81 |
| 17 | 0.8 | 1 | 70 |
| 18 | 0.8 | 2 | — |

This table shows the advantage of using more than one stage for removal of phenols from a phenol-containing naphtha stream. For example, a two stage process using a specific M/O value for each stage is capable of removing more of the phenols that a one stage process using an M/O value double that of the corresponding two stage process under the same conditions.

Each of the following examples was carried out by use of a small fixed-bed pyrolysis reactor equipped for controlling both liquid and gaseous reagent feeds. The reactor contained a preheater, a 15 inch long reactor tube fabricated from ½ inch O.D. stainless steel tubing, a furnace in which the reactor tube could be inserted, and a receiver and cold trap (accumulator section) for collecting liquid product and water. The preheater was used to preheat the helium sweep gas as well as to generate steam in those examples illustrating the present invention.

The metal phenates in the following examples were handled under an inert atmosphere of either helium or nitrogen to exclude both carbon dioxide and extraneous water. All transfers were carried out under nitrogen in a glove box. A small positive pressure of nitrogen gas was maintained during methylation reactions using a mineral oil bubbler as a pressure relief.

COMPARATIVE EXAMPLE F 1.30 g of calcium hydroxy phenate was placed in the reactor tube in a glove box under nitrogen. The reactor tube was connected to the preheater, capped, removed from the glove box, and installed in the furnace. A flow of helium sweep gas (100 ml/min.) was established and the accumulator was attached to the reactor tube. The preheater was heated to 250° C. and the reactor tube was heated to, and maintained at, 350° C. for 80 minutes, after which, it was cooled to room temperature under a flow of helium. The accumulator section was found to be empty. The reactor was capped and returned to the glove box where the residue was transferred to a reaction flask and methylated with 3.0 ml of iodomethane in 15 ml of N,N-dimethylformamide (DMF) solvent for 30 minutes at 60° C. to convert phenol moieties to anisole. Gas chromatographie analysis revealed that essentially all of the phenol moieties (99%) remained in the residue. Therefore, the calcium hydroxy phenate was thermally stable at 350° C., in the absence of steam, and did not release any phenols.

EXAMPLE 19

The procedure of Comparative Example F above was followed except the calcium hydroxy phenate was contacted with steam which was generated by feeding 1.87 ml of water into the preheater which was maintained at 250° C. This amount of water represented a 12 to 1 molar ratio of water to calcium hydroxy phenate and was fed to the preheater over a period of 10 minutes. The reactor tube was maintained at a temperature of 350° C. during the period of steam generation as well as for an additional 30 minutes to insure complete removal of volatiles from the residue. The reactor was then cooled, capped, and returned to the glove box. The methylation procedure of Comparative Example F was carried out on the residue. No anisole was detected in the product, hence, complete phenol liberation was obtained by steam stripping at 350° C. Analysis of the liquids in the accumulator by gas chromatography indicated a quantitative recovery of phenols from the calcium hydroxy phenate sample.

EXAMPLE 20 AND COMPARATIVE EXAMPLE G

The procedure of Example 19 above was followed except the temperature of the reactor tube was 150° C. for Comparative Example G and 250° C. for Example 20.

After steam stripping the phenate sample at 250° C., analysis of the residue and liquid indicated that 46% of the phenol moieties remained in the phenate residue while 54% were recovered as phenol.

After steam stripping the phenate sample at 150° C., analysis of the residue and liquid indicated that substantially all of the phenol moieties remained in the residue, while only a trace (<2%) were recovered as phenol.

The results of these two examples in combination with Example 19 above, in which steam stripping was carried out at a temperature of 350° C., illustrate that predetermined amounts of phenol can be recovered from a metal phenate by steam stripping the phenate at various temperatures for a given period of time and molar ratio of water to phenate.

The data of Examples 19, 20 and Comparative Example G are illustrated in FIG. 1 thereof.

EXAMPLES 21 AND 22

The procedure of Example 19 above was followed except the molar ratio of water to calcium hydroxy phenate was 4 to 1 for Example 22, and 9 to 1 for Example 21.

After steam stripping the phenate sample at 350° C. and molar ratio of water to phenate of 9 to 1, analysis of the residue and liquid indicated that approximately 75 wt.% of the phenol was recovered.

At a molar ratio of 4 to 1, approximately 35 wt.% of the phenol was recovered.

Thus, by adjusting the molar ratio of water to phenate in the steam stripping of a metal phenate at a given temperature and time period, one is able to recover a predetermined amount of phenol from the phenate.

Table V below sets forth the results of the above examples.

TABLE V

Wt. % Phenol Recovered From Calcium Hydroxy Phenate By Steam Stripping

| Example | Temp °C. | mol ratio $H_2O$ to phenate | Time in minutes | Wt. % phenol recovered |
|---|---|---|---|---|
| F | 350 | No $H_2O$ | 80 | 0 |
| 19 | 350 | 12:1 | 10 | 100 |
| 20 | 250 | 12:1 | 10 | 54 |
| G | 150 | 12:1 | 10 | <2 |
| 21 | 350 | 9:1 | 10 | 75 |
| 22 | 350 | 4:1 | 10 | 35 |

Figure 2:
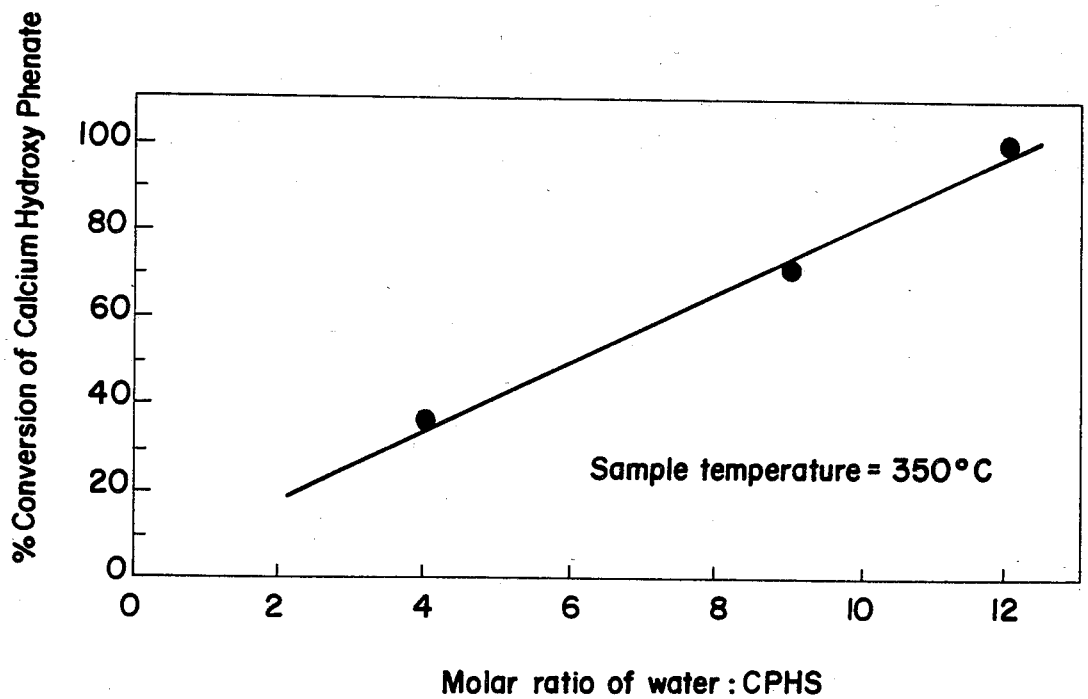
FIG. 2 illustrates that at a given temperature such as about 350° C. and in a given period of time, various amounts of phenol can be recovered from calcium hydroxy phenate by adjusting the molar ratio of water to calcium hydroxy phenate.

The data of this table are also shown in FIG. 2 hereof.

COMPARATIVE EXAMPLE H AND I

The procedure of Comparative Example F above was followed except for Comparative Example H, 1.30 g of sodium phenate was employed; and, for Comparative Example I, 1.30 g of potassium phenate was employed. Analysis of the residue from both of these examples indicated that no phenol was liberated and no liquid was found in the accumulator.

EXAMPLES 23 AND 24

The experimental procedure of Example 19 above was followed except that for Example 23 1.30 g of sodium phenate was employed and for Example 24 1.35 g of potassium phenate was employed. Analysis of the residue and liquid from each example revealed that 85 wt.% of phenol was recovered from sodium phenate and 86 wt.% of phenol was recovered from potassium phenate.

What is claimed is:

1. A process for recovering phenols from phenol-containing streams, having at least a sufficient amount of water, which method comprises:
   (a) contacting the phenol-containing stream with a metal composition consisting essentially of one or more oxides and/or hydroxides of metals capable of forming a metal phenate with phenols of the stream, wherein said contacting is performed below the lower of the following two temperatures (i) the decomposition temperature of the resulting metal phenate, or (ii) the temperature at which detrimental thermal degradation of the stream occurs,
   (b) separating the resulting metal phenate from the streams; and
   (c) treating the resulting metal phenate with steam at a temperature from about 250° C. to about 450° C., thereby producing phenols, and hydroxides of the metals of the phenate.

2. The process of claim 1 wherein the stream is a phenol containing hydrocarbonaceous stream.

3. The process of claim 2 wherein the hydrocarbonaceous stream is a coal liquid.

4. The process of claim 1 wherein the stream is contacted with one or more oxides and/or hydroxides of metals selected from the group consisting of alkali metals and alkaline-earth metals.

5. The process of claim 3 wherein the coal liquid is contacted with one or more oxides and/or hydroxides of metals selected from the group consisting of alkali metals and alkaline-earth metals.

6. The process of claim 5 wherein the coal liquid is contacted with sodium hydroxide.

7. The process of claim 5 wherein the coal liquid is contacted with calcium hydroxide.

8. The process of claim 6 wherein the resulting metal phenate is treated with steam at a temperature of about 350° C.

9. The process of claim 7 wherein the resulting hydroxy metal phenate is treated with steam at a temperature of about 350° C.

10. The process of claim 8 wherein the molar ratio of steam to phenate is at least about 10 to 1 and the temperature at which the phenate is contacted with steam is between about 300° C. to about 350° C.

11. The process of claim 9 wherein the molar ratio of steam to phenate is at least about 10 to 1 and the temperature at which the phenate is contacted with steam is between about 300° C. to about 350° C.

* * * * *